United States Patent
Berman et al.

(10) Patent No.: US 7,985,263 B2
(45) Date of Patent: *Jul. 26, 2011

(54) MEMBRANE FOR USE IN SUTURED OR SUTURELESS SURGICAL PROCEDURES

(75) Inventors: Andrew B. Berman, Flagstaff, AZ (US);
Thane L. Kranzer, Flaggstaff, AZ (US);
Dean R. Wentworth, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/624,877

(22) Filed: Nov. 24, 2009

(65) Prior Publication Data

US 2010/0106258 A1 Apr. 29, 2010

Related U.S. Application Data

(63) Continuation of application No. 10/133,653, filed on Apr. 25, 2002, now Pat. No. 7,641,958.

(51) Int. Cl.
*A61F 2/04* (2006.01)
*A61F 2/02* (2006.01)
*B32B 5/22* (2006.01)

(52) U.S. Cl. ........ 623/23.72; 623/23.73; 623/23.74; 623/23.76; 428/141; 428/143; 428/147; 428/156; 428/315.7

(58) Field of Classification Search .............. None
See application file for complete search history.

(56) References Cited

U.S. PATENT DOCUMENTS

| | | |
|---|---|---|
| 3,940,207 A | 2/1976 | Barkdoll |
| 4,193,138 A | 3/1980 | Okita |
| 4,196,256 A | 4/1980 | Eddy et al. |
| 4,304,010 A | 12/1981 | Mano |
| 4,482,516 A | 11/1984 | Bowman et al. |
| 4,501,783 A | 2/1985 | Hiragami et al. |
| 4,550,447 A | 11/1985 | Seiler, Jr. et al. |

(Continued)

FOREIGN PATENT DOCUMENTS

CA 894898 3/1972

(Continued)

OTHER PUBLICATIONS

Berman M et al. The Use of GORE-TEX® E-PTFE Bonded to Silicone Rubber as an Alloplastic Implant Material. Laryngoscope 1986; 96(5) 480-483.

(Continued)

*Primary Examiner* — D. Lawrence Tarazano
*Assistant Examiner* — Camie S Thompson
(74) *Attorney, Agent, or Firm* — Edward I. Amaya

(57) ABSTRACT

An improved, polymeric surgical membrane, which can be used in a variety of surgical procedures, such as sutured and sutureless duraplasty procedures. For sutureless applications, a textured, discontinuous, outer polymer layer is provided which encourages rapid incorporation and anchoring into surrounding tissue. In cooperation with the discontinuous first layer, a second elastomeric layer provides elasticity and resilience. A third barrier layer is provided to essentially eliminate adhesions and irritation to surrounding tissue. In those applications requiring anchoring sutures, the second elastomeric layer "self-seals" against the sutures, essentially eliminating the leakage of blood, cerebrospinal fluid, or other fluids. In addition, the composite structure of the present invention has a high degree of suture retention strength is polymeric with a high degree of biocompatibility, is thin and very flexible.

20 Claims, 14 Drawing Sheets

U.S. PATENT DOCUMENTS

| | | | |
|---|---|---|---|
| 4,552,816 A | 11/1985 | Spahic et al. | |
| 4,619,641 A | 10/1986 | Schanzer | |
| 4,647,416 A | 3/1987 | Seiler, Jr. et al. | |
| 4,692,369 A | 9/1987 | Nomi | |
| 4,713,070 A | 12/1987 | Mano | |
| 4,816,339 A | 3/1989 | Tu et al. | |
| 4,955,909 A | 9/1990 | Ersek et al. | |
| 5,002,572 A | 3/1991 | Picha | |
| 5,100,422 A | 3/1992 | Berguer et al. | |
| 5,152,782 A | 10/1992 | Kowligi et al. | |
| 5,207,709 A | 5/1993 | Picha | |
| 5,219,361 A | 6/1993 | von Recum et al. | |
| 5,236,453 A | 8/1993 | Picha | |
| 5,433,996 A | 7/1995 | Kranzler et al. | |
| 5,462,781 A | 10/1995 | Zukowski | |
| 5,529,830 A | 6/1996 | Dutta et al. | |
| 5,545,226 A | 8/1996 | Wingo et al. | |
| 5,571,182 A | 11/1996 | Ersek et al. | |
| 5,614,284 A * | 3/1997 | Kranzler et al. | 428/138 |
| 5,641,566 A * | 6/1997 | Kranzler et al. | 428/315.7 |
| 5,645,915 A * | 7/1997 | Kranzler et al. | 428/105 |
| 5,788,285 A | 8/1998 | Wicker | |
| 5,876,447 A | 3/1999 | Arnett | |
| 6,106,558 A | 8/2000 | Picha | |
| D445,188 S | 7/2001 | Walter | |
| 6,299,930 B1 | 10/2001 | Marotta et al. | |
| 6,319,264 B1 | 11/2001 | Tormala et al. | |
| 6,447,551 B1 | 9/2002 | Goldmann | |
| 6,514,291 B1 | 2/2003 | Yamauchi et al. | |
| 6,652,595 B1 | 11/2003 | Nicolo | |
| 6,709,732 B1 | 3/2004 | Graab et al. | |
| 6,786,910 B2 | 9/2004 | Fichtner et al. | |
| 6,913,626 B2 | 7/2005 | McGhan | |
| 7,641,958 B2 * | 1/2010 | Berman et al. | 428/143 |
| 2001/0056303 A1 | 12/2001 | Caneiro et al. | |

FOREIGN PATENT DOCUMENTS

| | | |
|---|---|---|
| CA | 2232617 | 3/1997 |
| EP | 0 352 972 | 1/1990 |
| JP | 54-74514 | 6/1979 |
| JP | 59-25725 | 2/1984 |
| JP | 63-007455 | 1/1988 |
| JP | 4-336072 | 11/1992 |
| JP | 10-278181 | 10/1998 |
| WO | 94/02185 | 2/1994 |
| WO | 94/19029 | 9/1994 |
| WO | 00/61045 | 10/2000 |
| WO | 03/026713 | 4/2003 |

OTHER PUBLICATIONS

DUALMESH® PLUS Biomaterial product brochure "A Legacy of Innovation in Hernia Repair" Jul. 2001.

GORE-TEX® Acuseal Cardiovascular Patch product brochure "We've closed the gap on suture line leakage!" Feb. 2000.

* cited by examiner

FIG. 3A
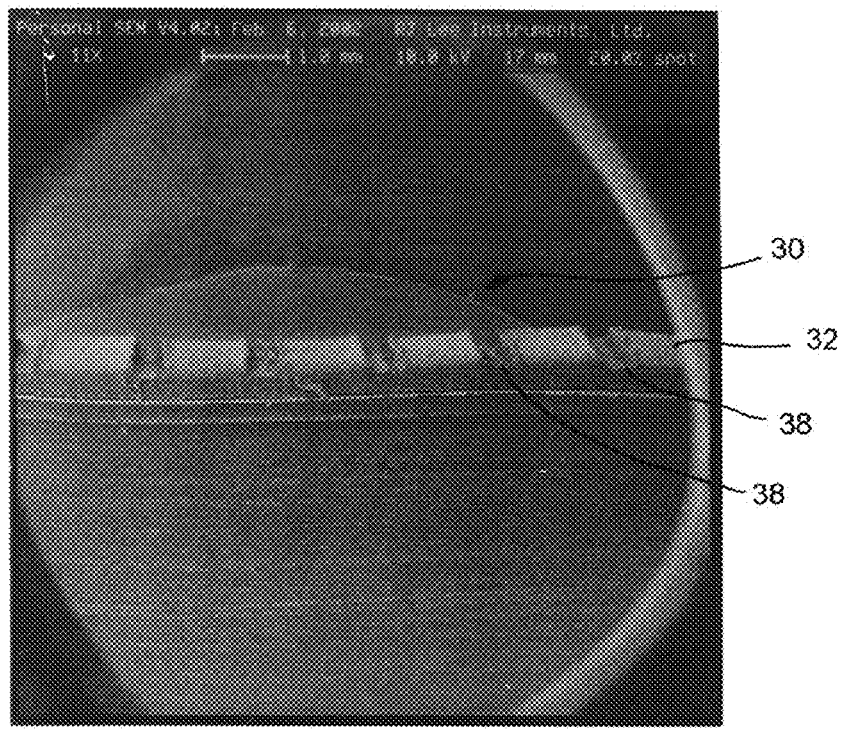
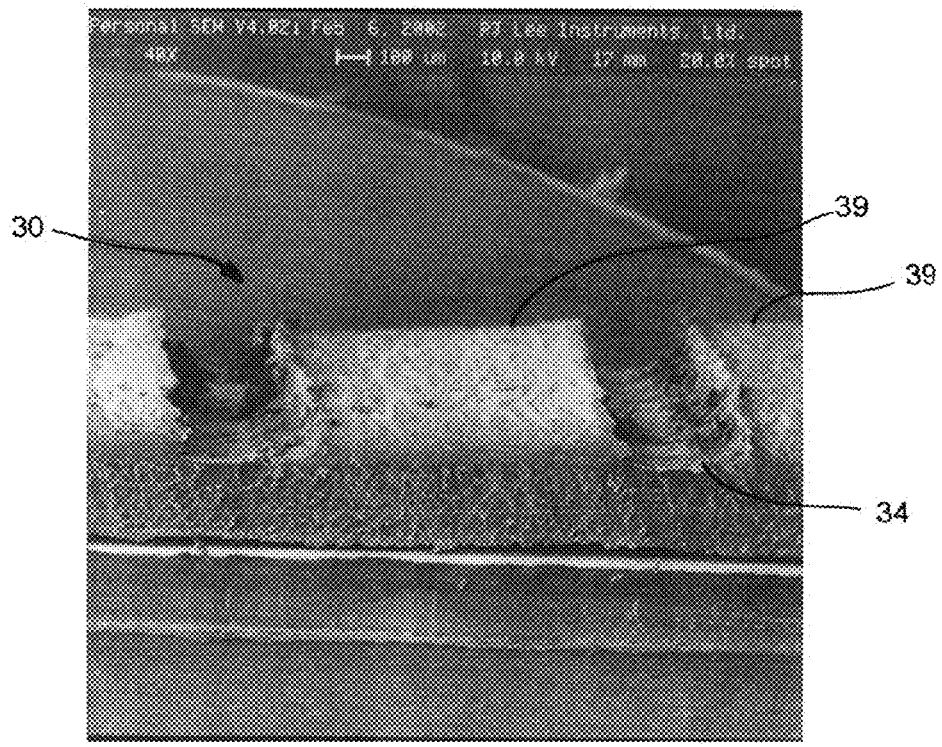
FIG. 3B

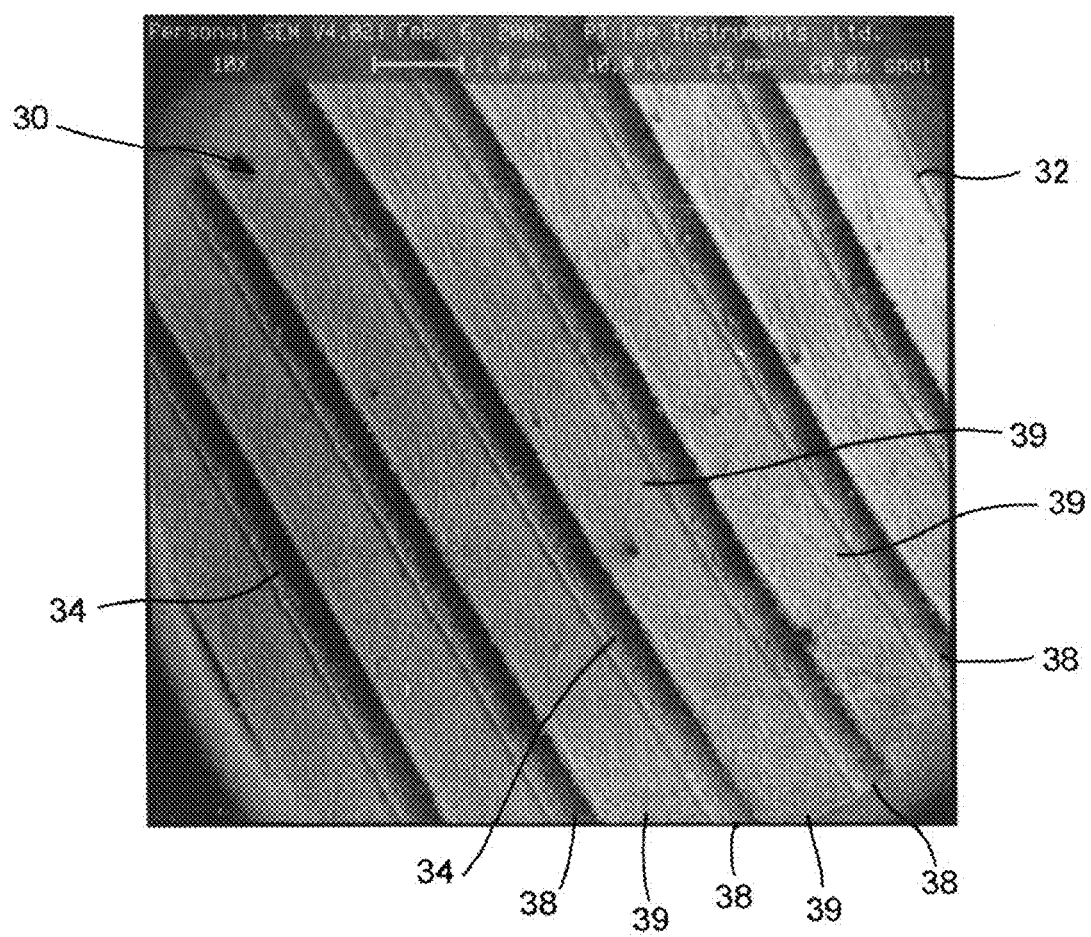

MEMBRANE FOR USE IN SUTURED OR SUTURELESS SURGICAL PROCEDURES

CROSS-REFERENCE TO RELATED APPLICATIONS

This is a continuation application of application Ser. No. 10/133,653 filed Apr. 25, 2002 now U.S. Pat. No. 7,641,958.

FIELD OF THE INVENTION

The present invention relates to implantable surgical membranes, such as those used in duraplasty procedures.

BACKGROUND OF THE INVENTION

The dura mater is the tough outermost layer of fibrous tissue that encapsulates the brain and spinal cord. It serves to protect and isolate the neural tissue and it serves as a watertight membrane that contains the cerebrospinal fluid (CSF). Repair or reconstruction of the dura mater may be necessary as a result of trauma or neurosurgical procedures requiring an incision or removal of a segment of the dura mater. Many different materials have been used to reconstruct the dura mater including various tissues from the patient's body or from animals and various synthetic materials. Various biological substances that have been tried include collagen sponges and membranes, fibrin film, and processed dermis.

Synthetic sheet materials used clinically include metal foils, natural rubber, silicone rubber, urethane, polyester and polyethylene. None of these has proven ideal for long term clinical success.

The ideal dura substitute should be nontoxic, biocompatible, non-immunogenic, free from foreign body reaction, free from the risk of disease transmission, watertight, able to self-seal, conformable, flexible, non-adherent, easy to use, and readily available. Only a few devices have come close to providing all of these attributes. Glutaraldehyde fixed bovine pericardium (such as materials sold under the DURA GUARD® trademark by BioVascular, Inc.) has been prepared commercially and meets many of the criteria. Although bovine pericardium has generally been used successfully, it can create adhesions, elicit an immunologic reaction and may expose patients to a possibility of disease transmission. Expanded polytetrafluoroethylene (such as material sold under the PRECLUDE® trademark by W.L. Gore & Associates, Inc.) has also been used quite successfully with the advantages being an absence of adhesions and having no risk of disease transmission. Although these materials have met with clinical success, they require suturing to the adjacent tissue to obtain a liquid tight closure. Suturing can take up to 30 minutes or more.

In recent years it has become known that some neurosurgical procedures do not require an immediate liquid tight closure and surgeons have shown some degree of success using porous collagen sponges in some applications (such as with material sold under the DURAGEN® trademark by Integra NeuroCare). Particularly near the top of the skull, the CSF pressure is relatively low so leakage is not as likely as would be the case at the base of the skull or in the spine where the pressure is higher. In areas of higher pressure, it is important to obtain an immediate liquid tight closure so that patients do not suffer from headaches and the possibility of infections secondary to CSF leakage. In light of these recent changes in neurosurgical practice, another ideal attribute of a dura substitute is the capability of being used with or without sutures depending on the requirements of the surgical procedure.

In addition to the requirements listed above for any dura substitute, there are several requirements for a material to be acceptable for use as a dura substitute that can be used with or without sutures. To be appropriate for use in sutured applications, the material itself should be liquid tight and have requisite strength to hold sutures to enable its use in high pressure applications. This eliminates collagen sponges since they are not liquid tight and they have no structural integrity once wetted. Also, a sutured membrane should be able to "seal" at the points where sutures penetrate the material. To facilitate the creation of a wrinkle- or pucker-free suture line, the ideal sutured material should be flexible, elastic, and resilient. For the material to also be used in sutureless applications, it should have the capability of being selectively incorporated with adjacent tissue, while preventing ingrowth or adhesion to neural tissue such as the brain or spinal cord.

A material such as PRECLUDE® Dura Substitute meets many of the requirements for a dura substitute but it is not suitable for use in sutureless applications because it does not allow for the tissue ingrowth or incorporation that will prevent migration. It also has limited elasticity, and therefore it is not easily conformed when sutured in place.

An improved material would have many of the attributes of PRECLUDE® Dura Substitute while allowing tissue ingrowth on the side facing away from the neural tissue as well as having greater elasticity. Used without sutures, the material would be tucked under the edges of the native dura with the tissue ingrowth surface facing away from the neural tissue. Implantation would be similar in both dura reconstruction procedures or flap closure procedures. When used in sutured applications, the material would be oriented in the same way but sutured to the edges of the native dura.

SUMMARY OF THE INVENTION

The present invention is an improved, polymeric dura substitute, which can be used in sutured and sutureless surgical procedures, such as in duraplasty procedures. For sutureless applications, the improved dura substitute has a textured, discontinuous, outer polymer layer on the side facing away from the neural tissue. This surface encourages rapid incorporation of adjacent tissue, which anchors the dura substitute without the need for sutures. Therefore, in sutureless applications, the interface between the dura substitute and the natural tissue creates a liquid tight seal and provides fixation. In cooperation with the discontinuous first layer, a second elastomeric layer provides elasticity and resilience. A third barrier layer is provided to essentially eliminate adhesions and irritation to neural tissue. In those applications requiring anchoring sutures, the second elastomeric layer "self-seals" against the sutures, essentially eliminating CSF leakage. In addition, the composite structure of the present invention has a high degree of suture retention strength, is polymeric with a high degree of biocompatibility and is thin and very flexible.

These and other benefits of the present invention will be appreciated from review of the following description.

DESCRIPTION OF THE DRAWINGS

The operation of the present invention should become apparent from the following description when considered in conjunction with the accompanying drawings, in which:

FIG. 3A is a cross sectional scanning electron micrograph, enlarged 11×, showing a three-quarter side perspective view of an article of the present invention.

FIG. 3B is a cross sectional scanning electron micrograph, enlarged 40×, showing a three-quarter side perspective view of an article of the present invention.

FIG. 3C is a scanning electron micrograph, enlarged 10×, showing a top view of an article of the present invention.

DETAILED DESCRIPTION OF DRAWINGS

Figure 1:
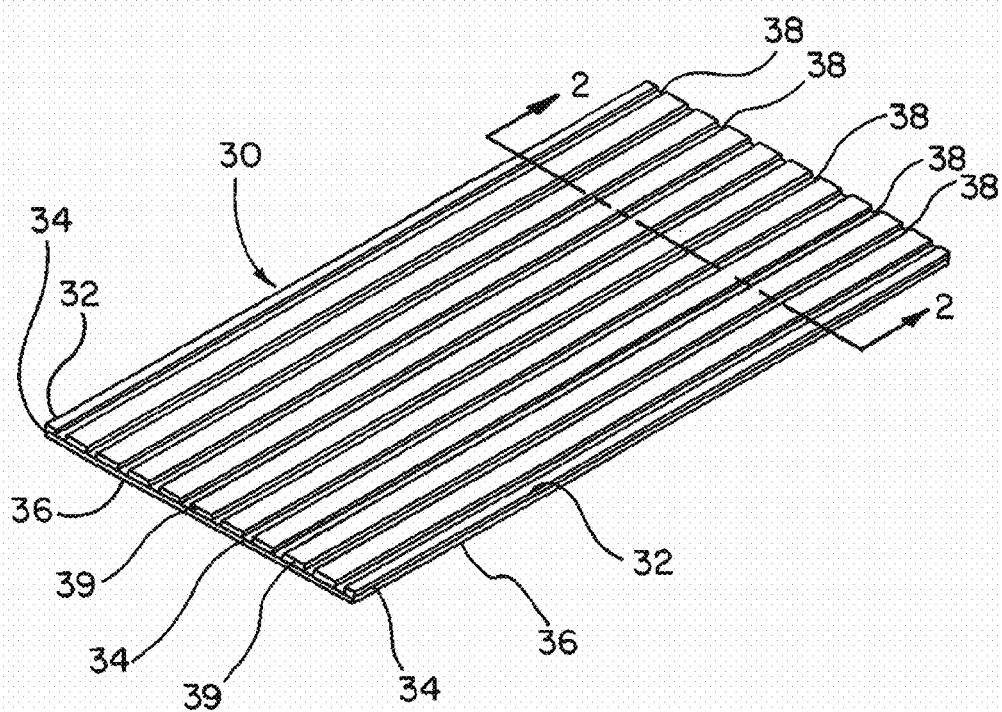
FIG. 1 is an isometric view of a three-layered article of the present invention showing a linear pattern of discontinuities in the first layer.

The following drawings and illustrations depict various embodiments of the present invention. Shown in FIG. 1 is an isometric view of an improved surgical membrane of the present invention. Shown is an article 30 of an improved surgical membrane, having a first, discontinuous layer 32, a second layer of an elastomer 34, and a third layer 36 tailored to prevent tissue ingrowth. The discontinuous first layer 32, when implanted against native tissue, encourages rapid tissue incorporation which anchors the surgical membrane. The third layer 36, provides a barrier which is structured to essentially eliminate adhesions and irritation to surrounding tissue. Also shown are several discontinuities 38, forming a pattern of discontinuities within the first layer 32. Shown is a "linear" pattern of discontinuities. A linear pattern comprises a series of essentially straight, parallel discontinuities. The first polymer layer with discontinuities is "macroscopically rough" and is comprised of adjacent polymer structures 39 which are separated from each other by the elastomeric layer 34.

One suitable application for the surgical membrane of the present invention is to deploy it as a dura substitute. In this application, the first layer 32 provides anchorage to the native dura. The third layer 36 provides protection against adhesion to the surrounding neural tissue.

Figure 2:
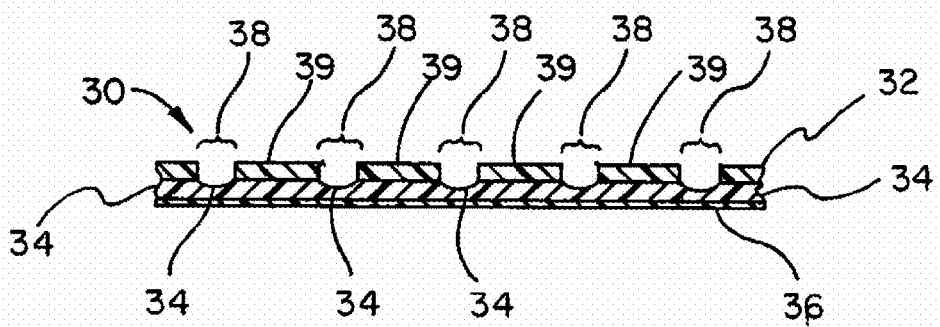
FIG. 2 is a cross sectional view of the three-layered article depicted in FIG. 1.

FIG. 2 is a cross sectional view of the improved surgical membrane as depicted in FIG. 1. Shown is a cross section of article 30 of an improved surgical membrane, having a first, discontinuous layer 32, a second continuous layer of an elastomer 34 and a third layer 36 tailored to prevent tissue ingrowth. Also shown are several discontinuities 38 within the first layer 32. The discontinuities 38, which expose the underlying elastomeric layer 34, form adjacent polymeric structures 39, which are separated from each other by the elastomer 34.

FIG. 3A is a scanning electron micrograph (SEM), showing a side and top perspective view similar to FIG. 2. Shown in FIG. 3A is article 30 of the improved surgical membrane of the present invention, having a first layer 32 with a series of discontinuities 38. FIG. 3B is a higher magnification of article 30 of the improved surgical membrane of the present invention, showing adjacent polymeric structures 39 which are separated from each other by the elastomer 34.

FIG. 3C is a scanning electron micrograph (SEM), showing a top view section of article 30 of the improved dura substitute of the present invention, having a first discontinuous layer 32. Also shown are several discontinuities 38 within the first layer 32. The discontinuities 38, which expose the underlying elastomeric layer 34, form adjacent polymeric structures 39, which are separated from each other by the elastomer 34.

With respect to terms used throughout this document, the following definitions apply:

A "continuous layer" is hereby defined as a layer characterized by an essentially uninterrupted presence so that an uninterrupted line can be defined across the material between any two points within the continuous layer.

A "discontinuous layer" is hereby defined as a layer which is interrupted with gaps, so that a continuous line cannot be defined across the material between any given two points within the overall layer.

A "discontinuity" is hereby defined as a gap or separation within a layer where, absent the discontinuity, the layer would be continuous.

A "pattern of discontinuities" is hereby defined as a repeating sequence of similar discontinuities or gaps within a layer.

"Adjacent polymeric structures" are hereby defined as at least two polymeric, three dimensional shapes which are separated by a common discontinuity or gap within the polymer, so that a continuous path cannot be defined between a point within the first polymeric structure and a point within the second polymeric structure.

"Adjacent polymeric structures separated from each other by an elastomer" is hereby defined as at least two adjacent polymeric structures which share a common border within the elastomer. An analogy might be two adjacent buildings (adjacent polymeric structures) separated by a concrete street (elastomeric layer).

A layer which is "macroscopically rough" is hereby defined as a layer having disruptions, gaps, changes in dimensions or surface topography which are large enough to be observed by the naked eye.

Figure 4:
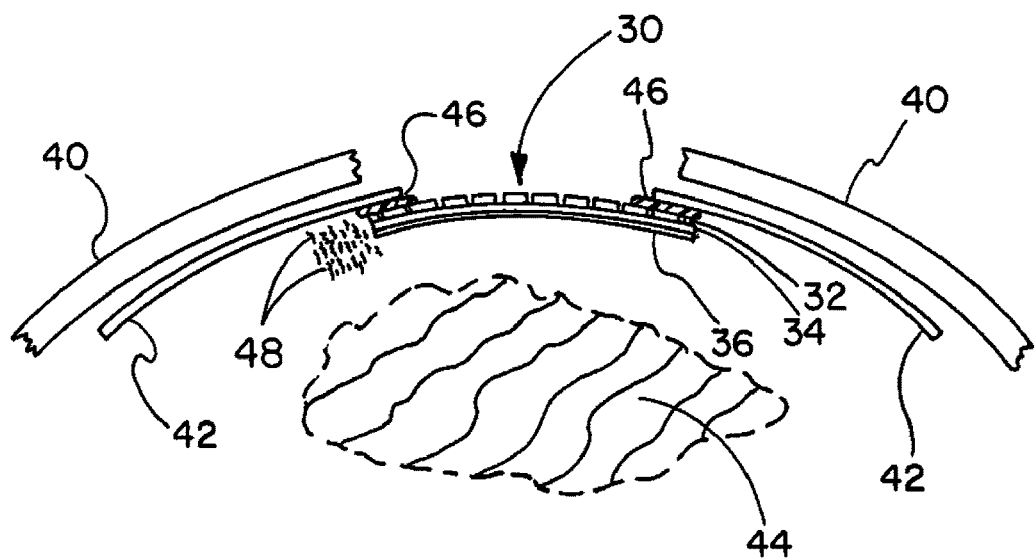
FIG. 4 is a cross sectional view of an implanted sheet article of the present invention, as used in a typical, sutureless, cranial duraplasty procedure.

FIG. 4 illustrates one application of the surgical membrane of the present invention in a cranial duraplasty. Shown is a cross sectional view of an access site of a typical cranial duraplasty procedure, completed without the use of sutures. Shown is bone 40, native dura 42, neural tissue 44, cerebral spinal fluid ("CSF") 48, along with an implanted article 30 of the present invention having first, second and third layers (32, 34, 36 respectively, as previously described). Shortly after implantation, the discontinuous first layer 32 incorporates and anchors to the native dura within the ingrowth regions 46. In suitable applications, this ingrowth and attachment provides an effective seal against CSF 48 leakage. The third, or barrier layer 36 of the article 30, is smooth and tailored to essentially eliminate irritation and adhesions onto adjacent neural tissue 44.

Figure 5:
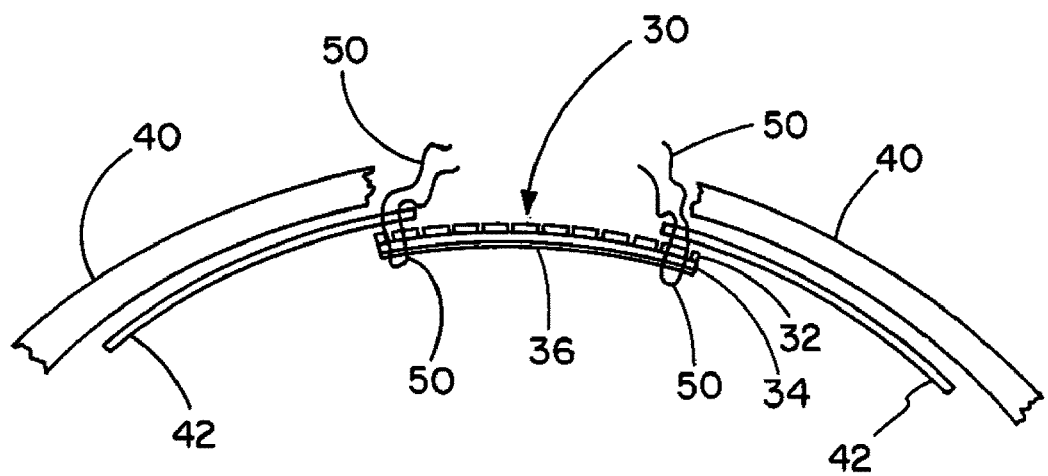
FIG. 5 is a cross sectional view of an implanted sheet article of the present invention, as used in a typical, sutured, cranial duraplasty procedure.

FIG. 5 is a cross sectional view of an access site of a typical cranial duraplasty procedure using sutures. Shown is bone 40, native dura 42, neural tissue 44, CSF 48, anchoring sutures 50 along with an implanted article 30 of the present invention having first second and third layers (32, 34, 36 respectively, as previously described). The flexibility of the first layer 32 (particularly as shown in FIG. 1) is enhanced by the discontinuities. The second elastomeric layer 34 adds resiliency, but does not significantly compromise flexibility. The combined flexibility and resiliency of the implanted article 30, facilitates the creation of a wrinkle- or pucker-free sutureline, which greatly reduces CSF leakage. The second elastomeric layer 34 also "self-seals" against the sutures 50, essentially eliminating the leakage of CSF 48.

Figure 6:
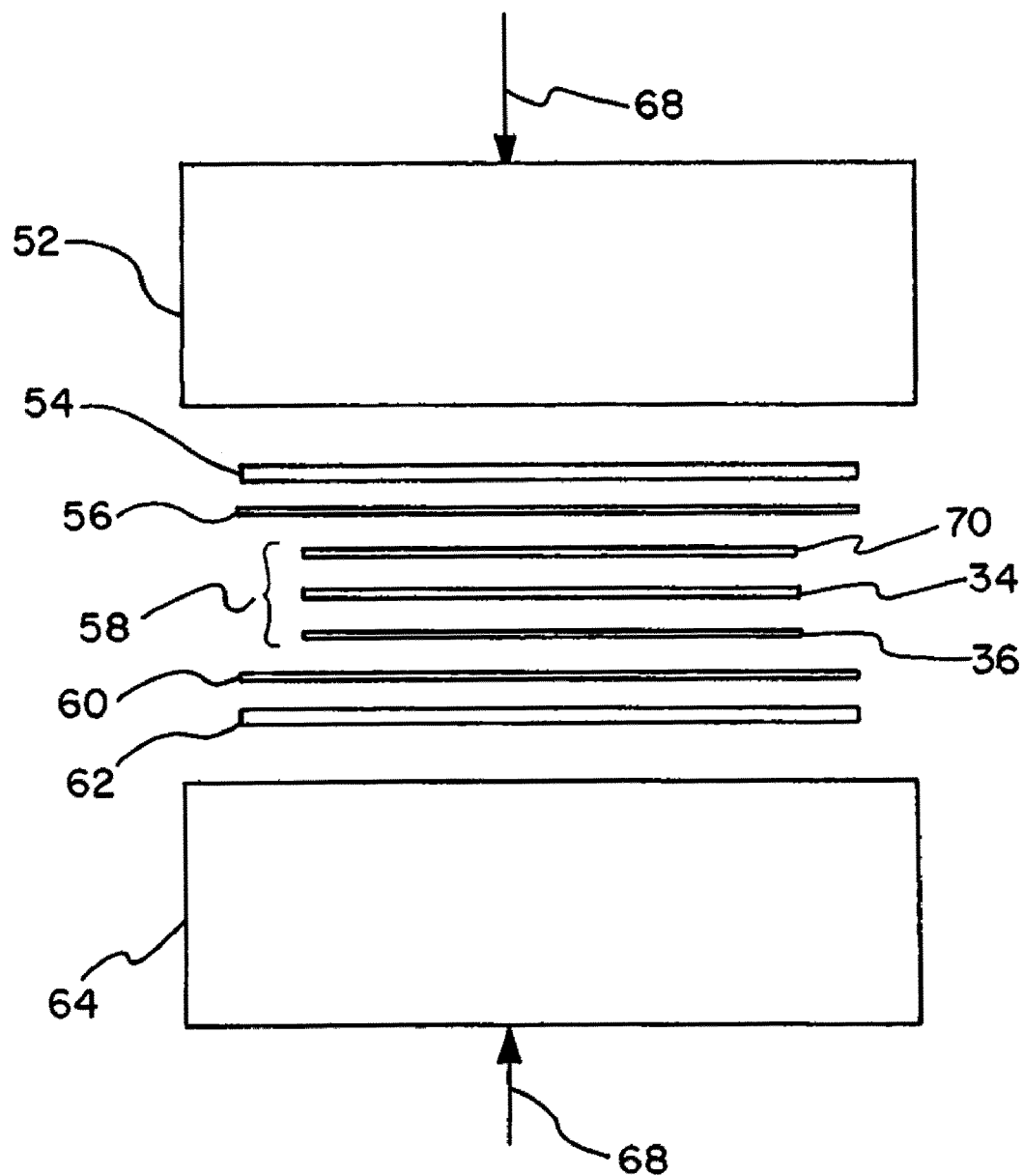
FIG. 6 is a side schematic view of a heated platen press used to produce a laminated sheet, as a precursor to the present invention.

Shown in FIG. 6 is a side view of a heated lamination press used to fabricate a multilayered article of the present invention. Shown is an upper heated platen 52, an upper stiffening plate 54, a first high temperature polymeric sheet 56, a series of sheets 58 to be laminated, a second high temperature polymeric sheet 60, a lower stiffening plate 62, and a lower heated platen 64. By applying a compressive load 68 to the heated platens for an amount of time, various sheet materials or combinations of sheets can be laminated together to form a laminated sheet.

A three-layer embodiment of the present invention can be manufactured by providing a first sheet layer 70, comprising expanded polytetrafluoroethylene (ePTFE), approximately 0.16 mm thick, having an average fibril length of greater than about 10 um, processed in accordance with U.S. Pat. No. 4,482,516. The first layer 70 is preferably "continuous", and therefore there are no significant "discontinuities" separating polymer structures. Various patterns of discontinuities can be incorporated into the laminated structure during subsequent processing. A second elastomeric sheet layer 34 is positioned as shown in FIG. 6. The elastomeric layer can be a thermoplastic or a thermoset and is preferably a biocompatible elastomer, such as one comprising fluoropolymer. Certain thermoset elastomers may laminated without the use of heat and may be cured at ambient temperature with minimal pressure. A third sheet layer 36 is provided, comprising ePTFE, approximately 0.05 mm thick, having an average fibril length of less than about 5 µm, processed in accordance with U.S. Pat. No. 4,482,516. The short fibril length and small pore size significantly prohibits cellular ingrowth after implantation, thereby providing a barrier, which reduces or eliminates adhesions onto adjacent tissues.

One sheet material that functions well with the present invention comprises a three-layer composite constructed by providing a first sheet layer of expanded polytetrafluoroethylene (ePTFE), approximately 0.1 to 0.5 mm thick, having an average fibril length of greater than about 10 µm, processed in accordance with U.S. Pat. No. 4,482,516. A second fluoroelastomeric sheet layer comprised of a thermoplastic copolymer of tetrafluoroethylene (TFE) and perfluoro(methyl vinyl ether) (PMVE), having attributes as described in Table 1, below. The crumb form of the copolymer may be compression molded at an elevated temperature (e.g., about 250° C.) to form a sheet about 0.1 to 0.5 mm thick. A third sheet layer comprised of ePTFE, approximately 0.01 to 0.1 mm thick, having an average fibril length of less than about 5 µm, processed in accordance with U.S. Pat. No. 4,482,516. The three sheet materials are aligned together as shown in FIG. 6 (items 58, 70, 34 and 36) and placed between layers of high temperature plastic and aluminum plates (items 54, 56, 60 and 62). The aluminum plates can be formed in any desired dimensions. The high temperature plastic sheets are preferably about 0.05 mm thick and comprise KAPTON® polyimide (E.I. DuPont de Nemours, Wilmington, Del.) or similar material. The assembly is then laminated as described in FIG. 6 for about 5 minutes, at about 200° C., with a pressure of about 0.5 MPa (80 lb/in$^2$). The laminated sheet is then positioned onto a laser (as described in FIG. 7) to create a pattern of discontinuities and macroscopic roughness into the first layer of the laminated sheet. The laminated sheet periphery is constrained by a ringed pin fixture or similar apparatus. The laser can be adjusted to have an output of about 140 to 400 W, a relatively focused beam, and a cutting traverse speed of about 100 to 200 cm/sec. A suitable pattern of discontinuities created with this process is shown in FIG. 1. The discontinuities may be any desired width and spacing from center to center. The completed article may be any combined thickness of its component parts, such as from less than about 0.1 mm to more than 1 mm.

TABLE 1

| Characteristic | Target |
| --- | --- |
| PMVE wt % | 50-70% |
| TFE wt % | 30-50% |
| 100% Secant Modulus* | $1.0 < X < 4.0$ MPa |

TABLE 1-continued

| Characteristic | Target |
| --- | --- |
| Softening Temperature | <275° C. |
| Thermal Degradation Temperature | >300° C. |
| Melt Flow Index** | >2.0 |
| Durometer | 60-80 Shore A |

*as per ASTM D412-98, using ½ scale Type IV dogbone with 250 mm/min crosshead speed and approximately 40 mm grip separation.
**grams per 10 minutes, 10 kg, 325° C.

Various materials and configurations can be adapted to create various laminated sheets. For example the continuous first layer 70 can have a thickness ranging from about 0.05 mm to about 0.4 mm. For example a thickness of a first layer can be about 0.05 mm, about 0.1 mm, about 0.15 mm, about 0.25 mm, about 0.3 mm, about 0.35 mm, or about 0.4 mm. The continuous first layer 70 can have a preferred thickness ranging from about 0.12 mm to about 0.22 mm. For example, a preferred thickness of a first layer can be about 0.14 mm, about 0.16 mm, about 0.18 mm, about 0.2 mm or about 0.22 mm. The continuous first layer 70 can have a most preferred thickness of about 0.17 mm. For porous sheets, the porosity or microstructure can be altered to enhance various mechanical properties or biological responses, as required for specific applications.

The second elastomeric sheet layer 34 can comprise a thermoplastic, a thermoset, or other material. Suitable elastic materials include, but are not limited to organosilicon polymers, polyurethanes, and various fluoropolymers. The second elastomeric layer 34 can have a thickness ranging from about 0.05 mm to about 0.4 mm. For example, a thickness of a second elastomeric layer can be about 0.05 mm, about 0.1 mm, about 0.15 mm, about 0.25 mm, about 0.3 mm, about 0.35 mm or about 0.4 mm. The second elastomeric layer 34 can have a preferred thickness ranging from about 0.15 mm to about 0.25 mm. For example, a preferred thickness of the second elastomeric layer can be about 0.15 mm, about 0.17 mm, about 0.19 mm, about 0.21 mm, about 0.23 mm or about 0.25 mm. The second elastomeric layer can have a most preferred thickness of about 0.2 mm.

The third sheet layer 36 can have a thickness ranging from about 0.02 mm to about 0.16 mm. For example, a thickness of a third layer 36 can be about 0.02 mm, about 0.08 mm, about 0.1 mm, about 0.12 mm, about 0.14 mm, or about 0.16 mm. The third sheet layer can have a preferred thickness ranging from about 0.03 mm to about 0.07 mm. For example, a preferred thickness of a third layer can be about 0.03 mm, about 0.04 mm, about 0.06 mm, or about 0.07 mm. The third layer 36 can have a most preferred thickness of about 0.05 mm.

For porous sheets, the porosity or microstructure can be altered to enhance various mechanical properties or biological responses, as required for specific applications. Other materials suitable for a specific layer, include but are not limited to polyethylene, nylon polyamide, DACRON®, polyvinylchloride, polyglycolic acid, and polylactic acid. Layers can have an open mesh, woven structure or perforated structure and be combined with various materials to produce desired physical attributes.

Figure 7:
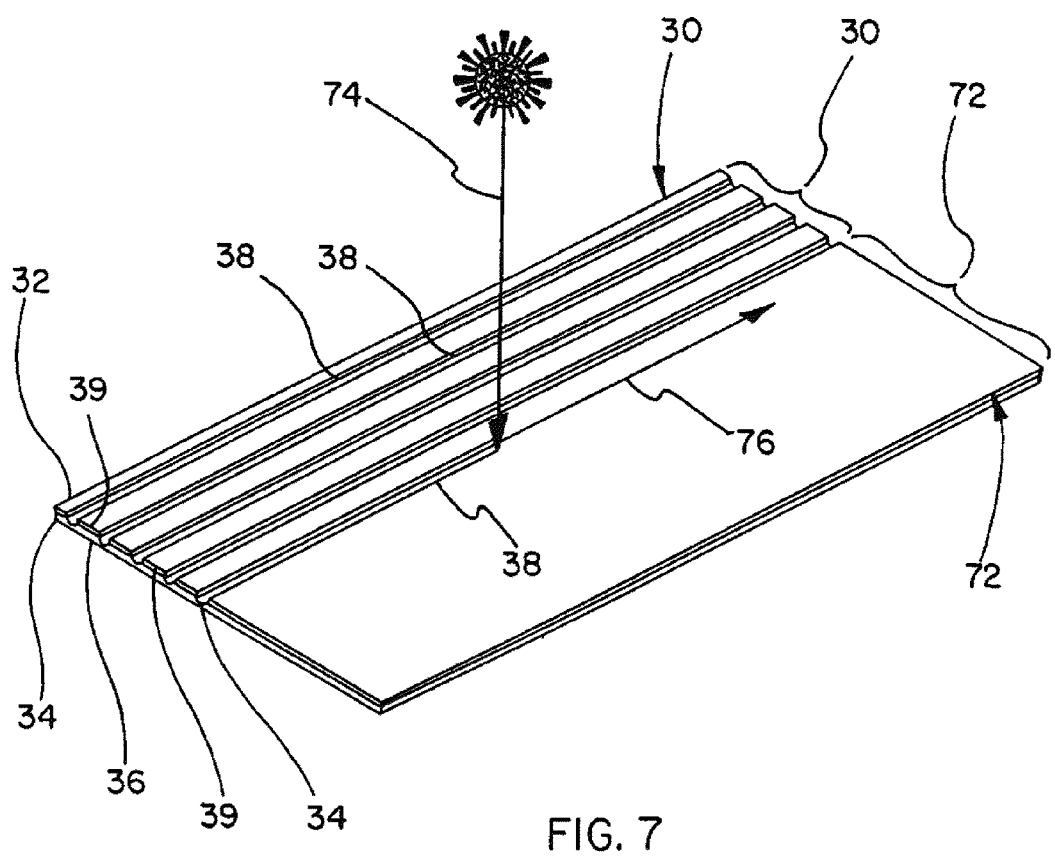
FIG. 7 is an isometric view of a laser system used to create discontinuities and macro-roughness into a first layer of a laminated sheet, creating a preferred embodiment of the present invention.

The lamination process described in FIG. 6 produces a laminated sheet. This laminated sheet can then be altered to impart discontinuities and macroscopic roughness into an outer layer of the laminated sheet. FIG. 7 describes a preferred laser treatment, used to impart discontinuities and macroscopic roughness into an outer layer of the laminated sheet. Shown is a partial laminated sheet 72 produced in accordance with the lamination process previously described. A laser 74 is traversed in direction 76 across the laminated sheet 72, cutting and creating discontinuities 38 into the first layer 32. The discontinuities create adjacent polymeric structures 39, which are separated from each other by the elastomer 34. By creating multiple discontinuities, an article of the present invention 30 (as shown in FIG. 1) is produced. The outer first layer is discontinuous and macroscopically rough. The laser beam 74 width, focal distance, pulse rate, pulse duration and traversing speed are adjusted to cut and remove material substantially from the first polymeric layer 32. Minimal material is removed from the elastomeric layer 34.

Various patterns of discontinuities and adjacent polymeric structures can be incorporated into articles of the present invention. The patterns of discontinuities can be used to create adjacent polymer structures, which are separated from each other by the elastomer. The width of a discontinuity can range from about 0.1 mm to over 4 mm. For example, a width of a discontinuity can be about 0.3 mm, about 1 mm, about 2 mm, about 3 mm, or about 4 mm, or more. Preferably a width of a discontinuity can be about 0.4 mm, about 0.6 mm or about 0.8 mm. A width of a discontinuity is most preferably about 0.5 mm. The spacing between centerlines of adjacent discontinuities can range from about 0.5 mm to about 5 mm or more. For example, a spacing between centerlines of adjacent discontinuities can be about 1 mm, about 2 mm, about 3 mm, about 4 mm, or about 5 mm, or more. Preferably, the spacing between centerlines of adjacent discontinuities can be about 1.5 mm, about 2 mm, or about 2.5 mm. Most preferably, the spacing between centerlines of adjacent discontinuities can be about 1.2 mm, about 1.3 mm, or about 1.4 mm.

Figure 8:
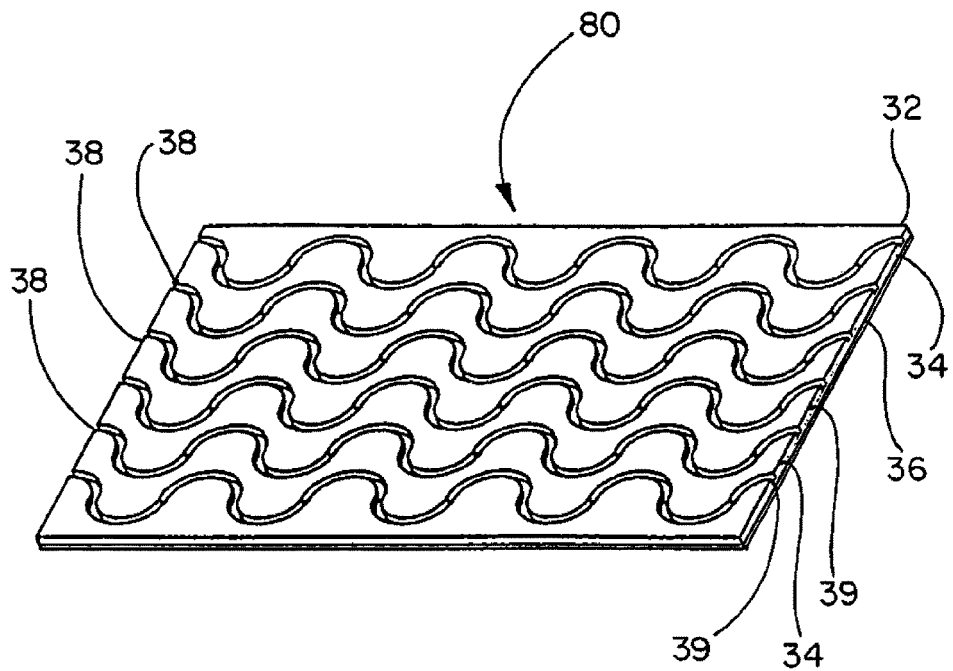
FIG. 8 is an isometric view of an alternate embodiment of a sheet article of the present invention having a serpentine pattern of discontinuities.

Shown in FIGS. 8 through 11 are examples of various patterns of discontinuities and adjacent polymer structures that can be incorporated in the surgical membrane of the present invention. Shown in FIG. 8 is an isometric view of an alternate configuration of a sheet article 80 of the present invention. Shown is a "serpentine" pattern of discontinuities 38. Also shown are adjacent polymer structures 39 separated by an elastomer 34.

Figure 9:
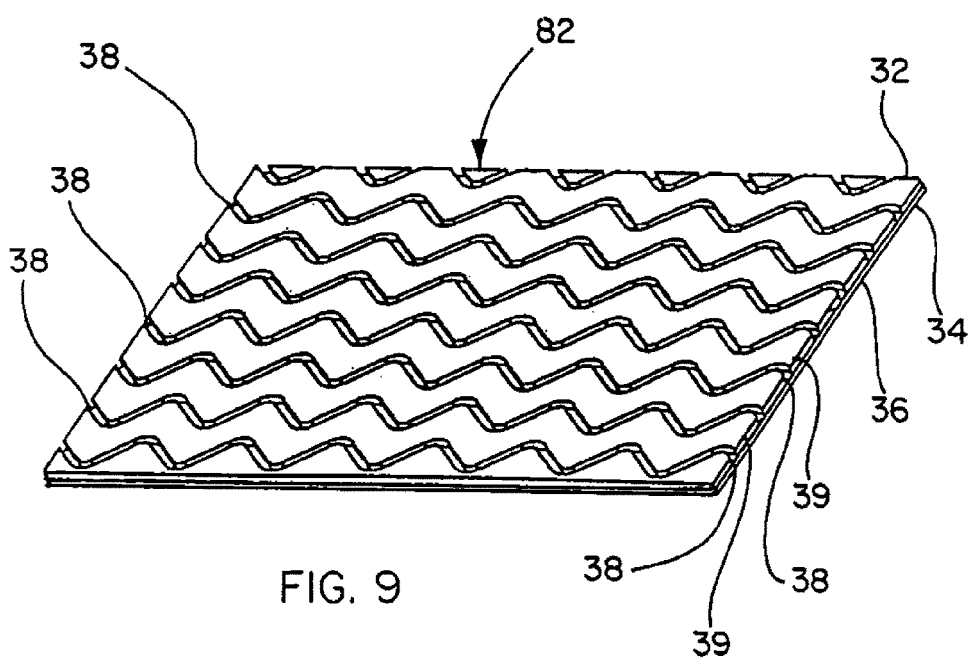
FIG. 9 is an isometric view of an alternate embodiment of a sheet article of the present invention having a zigzag pattern of discontinuities.

Shown in FIG. 9 is an isometric view of an alternate configuration of a sheet article 82 of the present invention. Shown is a "zigzag" pattern of discontinuities 38. Also shown are adjacent polymer structures 39 separated by an elastomer 34.

Figure 10:
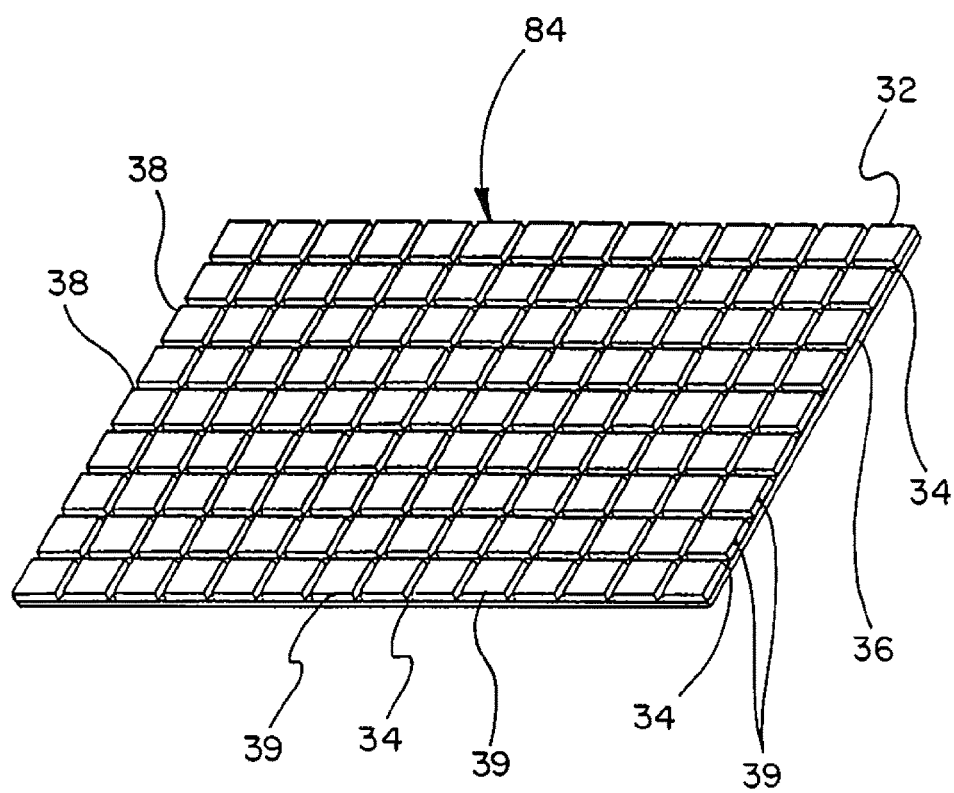
FIG. 10 is an isometric view of an alternate embodiment of a sheet article of the present invention having a crosshatch pattern of discontinuities.

Shown in FIG. 10 is an isometric view of an alternate configuration of a sheet article 84 of the present invention. Shown is a "crosshatch" pattern of discontinuities 38. Also shown are adjacent polymer structures 39 separated by an elastomer 34.

Figure 11:
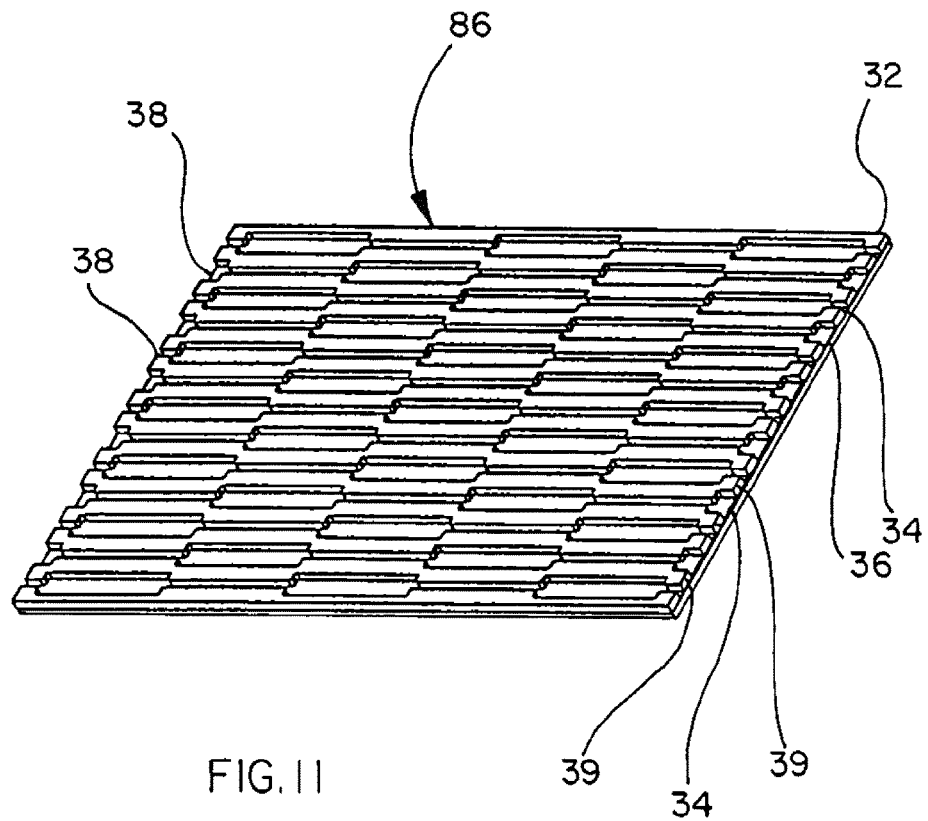
FIG. 11 is an isometric view of an alternate embodiment of a sheet article of the present invention having an interlocking pattern of discontinuities.

Shown in FIG. 11 is an isometric view of an alternate configuration of a sheet article 86 of the present invention. Shown is an "interlocking" pattern of discontinuities 38. Also shown are adjacent polymer structures 39 separated by an elastomer 34.

Figure 12:
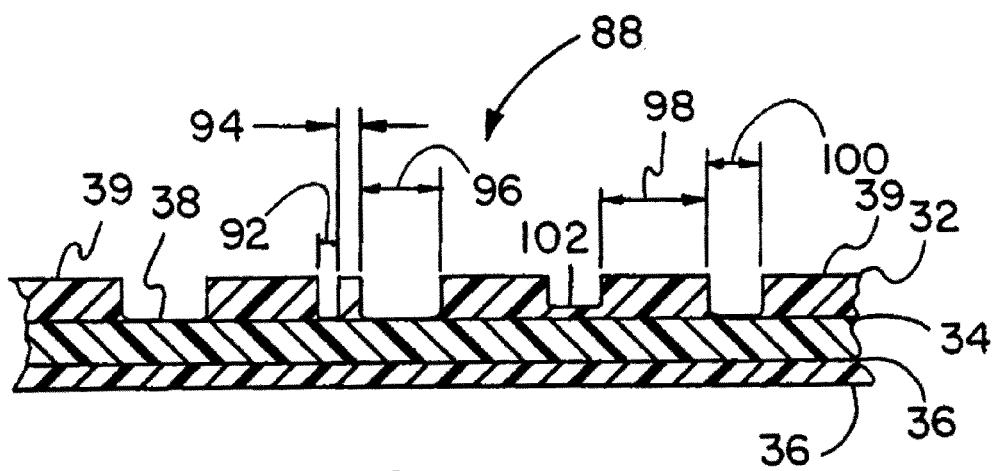
FIG. 12 is a cross sectional view of an alternate, three-layered embodiment of the present invention showing a micro-rough first layer having adjacent polymeric structures with varying widths, discontinuities with varying widths, and discontinuities that have not fully penetrated the first layer.

In addition to having alternate patterns of discontinuities, articles of the present invention can have various combinations and configurations of laminated layers, best illustrated in cross sectional views similar to FIG. 2. Shown in FIG. 12 is a cross sectional view of an article 88 of the present invention. Shown is a first, discontinuous layer 32, a second layer of an elastomer 34, a third layer 36 and discontinuities 38 within the first layer 32. Also shown are various widths 92, 96 and 100 of discontinuities 38. Also shown are various widths 94 and 98 of adjacent polymer structures 39. Also shown is an alternate configuration in which a portion 102 of the first layer 32 remains within a discontinuity. To create such a remaining portion 102, the laser parameters were adjusted so that the entire depth of the first layer was not removed.

Figure 13:
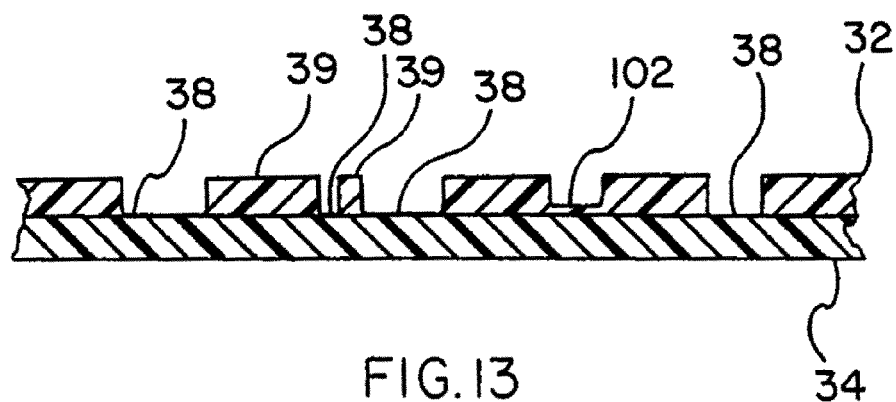
FIG. 13 is a cross sectional view of an alternate two-layered embodiment of the present invention showing a macro-rough first layer having adjacent polymeric structures with varying widths, discontinuities with varying widths, and discontinuities that have not fully penetrated the first layer.

Shown in FIG. 13 is a cross sectional view an alternate embodiment of an article 104 of the present invention. Shown is a two-layer configuration having a first layer 32, a second elastomeric layer 34, discontinuities 38, adjacent polymeric structures 39 separated from each other by the elastomeric layer 34. Also shown is a portion 102 of the first layer remaining in a discontinuity.

Figure 14:
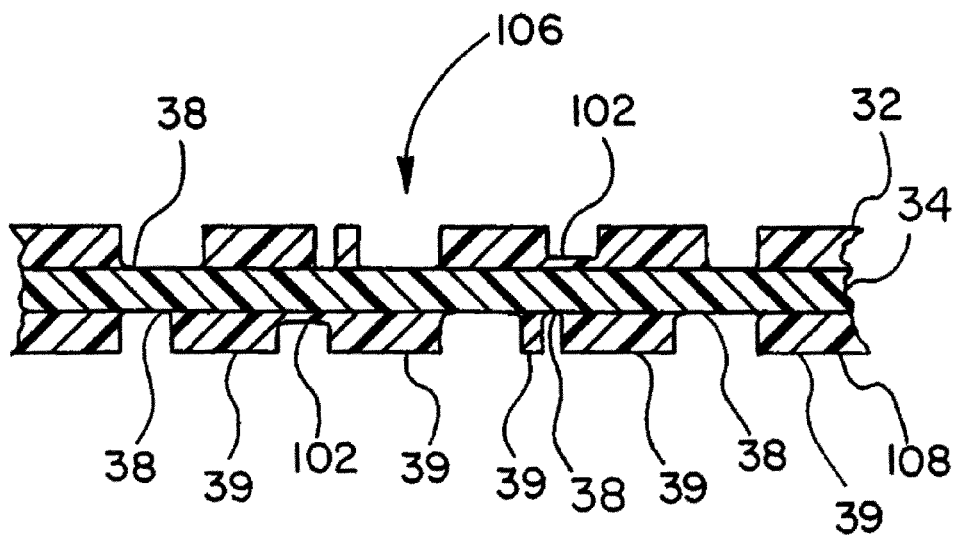
FIG. 14 is a cross sectional view of an alternate three-layered embodiment of the present invention showing macro-rough first and third layers having adjacent polymeric structures with varying widths, discontinuities with varying widths, and discontinuities that have not fully penetrated the first or third layer.

Shown in FIG. 14 is a cross sectional view of an alternate embodiment of an article 106 of the present invention. Shown is a three-layer configuration having a first layer 32, a second elastomeric layer 34, and a third layer 108 which has a configuration similar to that of the first layer 32. Shown are discontinuities 38 and adjacent polymeric structures 39 separated from each other by an elastomer 34. Also shown is a portion 102 of the first layer 32 or of the third layer 108 remaining in a discontinuity. The third layer can have a pattern of discontinuities, which can be the same or different from the pattern in the first layer.

Figure 15:
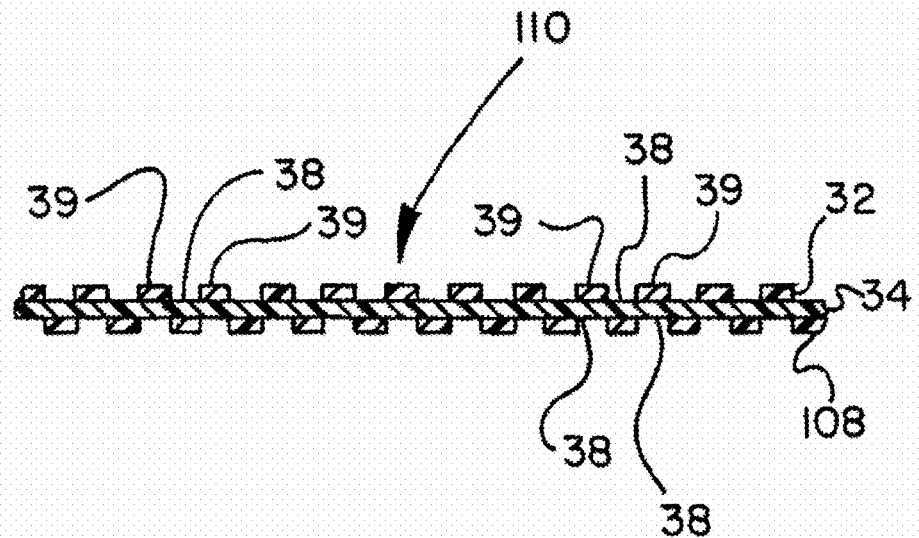
FIG. 15 is a cross sectional view of an alternate three-layered embodiment of the present invention showing staggered adjacent polymeric structures within the first and third layers.

Shown in FIG. 15 is a cross sectional view of an alternate embodiment of an article 110 of the present invention. Shown is a three-layer configuration having a first layer 32, a second elastomeric layer 34, and a third layer 108 which has a configuration similar to that of the first layer 32. The patterns of discontinuities in layers 32 and 108 are offset so that a discontinuity 38 in layer 32 is approximately aligned to a polymeric structure 39 in layer 108.

Figure 16:
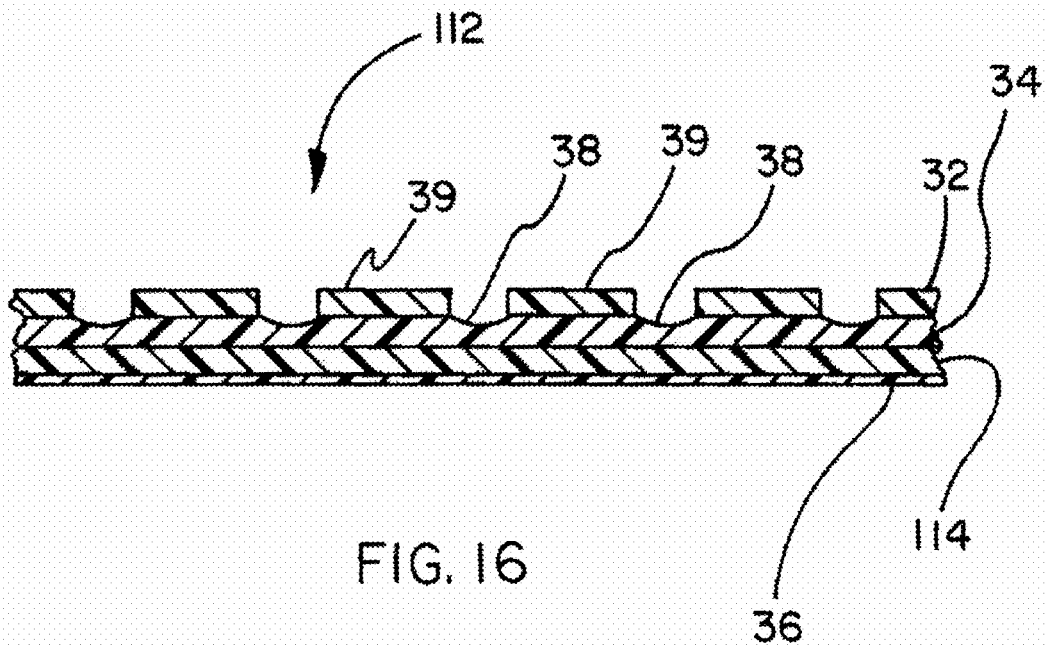
FIG. 16 is a cross sectional view of an alternate four-layered embodiment of the present invention showing adjacent polymeric structures and discontinuities within the first layer.

Shown in FIG. 16 is a cross sectional view of a four-layer embodiment of an article 112 of the present invention. Shown is a first layer 32, a second elastomeric layer 34, a third layer 36, and a fourth layer 114. The fourth layer 114 can be comprised of a variety of elastomers or other materials. The mechanical properties of the material of the fourth layer 114 can be selected to provide specific attributes to the article 112.

In addition to having various patterns of discontinuities or combinations and configurations of laminated layers, articles of the present invention can incorporate a wide range of different materials. For example, various layers can be comprised of bioresorbable polymers such as polyglycolic acid and polylactic acid. Various layers of materials, incorporated into articles of the present invention, can be coated or filled with pharmaceutical agents and drugs.

Without intending to limit the present invention, the following examples specify how the present invention can be made and tested.

EXAMPLE 1

A three-layer embodiment of the present invention, approximately 7.5 cm (3") by 10 cm (4"), was constructed by providing a first sheet layer comprised of expanded polytetrafluoroethylene (ePTFE), approximately 0.17 mm thick, having an average fibril length of greater than about 10 µm, processed in accordance with U.S. Pat. No. 4,482,516. A second fluoro-elastomeric sheet layer was comprised of a thermoplastic copolymer of tetrafluoroethylene (TFE) and perfluoro(methyl vinyl ether) (PMVE), having attributes as described in Table 2, below. The crumb form of the copolymer was compression molded at about 250° C. to form a sheet about 0.2 mm (0.008") thick. A third sheet layer was provided, comprised of ePTFE, approximately 0.05 mm thick, having an average fibril length of less than about 5 µm, processed in accordance with U.S. Pat. No. 4,482,516. The three sheet materials were aligned together as shown in FIG. 6 (items 58, 70, 34 and 36) and placed between layers of high temperature plastic and aluminum plates (items 54, 56, 60 and 62). The aluminum plates were approximately 23 cm (9") square. The high temperature plastic sheets approximately 0.05 mm (0.002") were comprised of KAPTON® polyimide (E.I. DuPont de Nemours, Wilmington, Del.). The assembly was then laminated as described in FIG. 6 for about 5 minutes, at about 200° C. with a pressure of about 0.5 MPa (80 lb/in$^2$). The laminated sheet was then positioned onto a laser (as described in FIG. 7) to create a pattern of discontinuities and macroscopic roughness into the first layer of the laminated sheet. The laminated sheet periphery was constrained by a ringed pin fixture. The laser was a Laser Machining Inc. (Somerset, Wis.), $CO_2$ Eagle 500 Laser with Lightening Bolt Control Software. The laser was adjusted to have an output of about 160 W, a −0.4125 focus, cutting traverse speed of about 200 cm/sec (80 in/sec). The pattern of discontinuities was as shown in FIG. 1. The discontinuities were approximately 0.5 mm (0.02") wide and spaced approximately 0.13 mm (0.05") from center to center. The completed article was about 0.4 mm (0.016") thick. It should be appreciated by one skilled in the art that laser settings may vary between two lasers of the same make and model. Exact settings may have to be adjusted to achieve the desired results.

TABLE 2

| Characteristic | Target |
| --- | --- |
| PMVE wt % | about 60% |
| TFE wt % | about 40% |
| 100% Secant Modulus* | about 2.1-2.2 MPa |
| Softening Temperature | <275° C. |
| Thermal Degradation Temperature | >300° C. |
| Melt Flow Index** | >2.0 |
| Durometer | 60-80 Shore A |

*as per ASTM D412-98, using ½ scale Type IV dogbone with 250 mm/min crosshead speed and approximately 40 mm grip separation.
**grams per 10 minutes, 10 kg, 325° C.

EXAMPLE 2

A three-layer embodiment of the present invention, approximately 7.5 cm (3") by 10 cm (4"), was constructed by providing first and third sheet layers comprised of ePTFE according to Example 1. The second elastomeric layer was comprised of a thermoplastic polyurethane, available as Pellethane 80A available from Dow Chemical Co. (Midland, Mich.). The resin was desiccated at about 214° C. for about 12 hours. About 14 grams of the resin was then compression molded at about 190° C. to form a sheet, approximately 20 cm (8") in diameter with a thickness of about 0.2 mm (0.008"). A laminated sheet was then formed in accordance with Example 1. The laminated sheet was then laser processed according to Example 1. The completed article was about 0.4 mm (0.016") thick.

EXAMPLE 3

A three-layer embodiment of the present invention, approximately 7.5 cm (3") by 10 cm (4"), was constructed by providing first and third sheet layers comprised of ePTFE according to Example 1. The second elastomeric layer was comprised of a thermoplastic silicone polycarbonate urethane, available as CARBOSIL™ 20 90A available from The Polymer Technology Group Inc. (Berkeley, Calif.). The resin was desiccated at about 214° C. for about 12 hours. About 14 grams of the resin was then compression molded at about 190° C. to form a sheet, approximately 20 cm (8") in diameter with a thickness of about 0.2 mm (0.008"). A laminated sheet was then formed in accordance with Example 1. The laminated sheet was then laser processed according to Example 1. The completed article was about 0.4 mm (0.016") thick.

EXAMPLE 4

A three-layer embodiment of the present invention, approximately 7.5 cm (3") by 10 cm (4"), was constructed by providing first and third sheet layers comprised of ePTFE according to Example 1. The second elastomeric layer was comprised of a thermoset silicone, available as NUSIL R-1140 RTV Silicone Adhesive, available from Nusil Technology (Carpinteria, Calif.). A laminated sheet was then formed by spreading a thin layer of the silicone adhesive onto the third sheet layer of ePTFE. The first sheet layer of ePTFE was then placed and aligned onto the adhesive coated third layer. Sheets of KAPTON® polyimide (according to Example 1) were placed onto the outer sheet layers as shown in FIG. 6. Two steel plates approximately 15 cm (6") square, by about 6 mm (0.25") thick were placed onto the KAPTON® sheets and used as weights during an ambient cure of about 4 hours. The cured, laminated sheet was then laser processed according to Example 1. The completed article was about 0.4 mm (0.016") thick.

EXAMPLE 5

A suturehole leak test was performed on articles of the present invention, produced according to Example 1. A suture hole leak rate test apparatus is described in FIGS. 17, 18 and 19.

Figure 17:
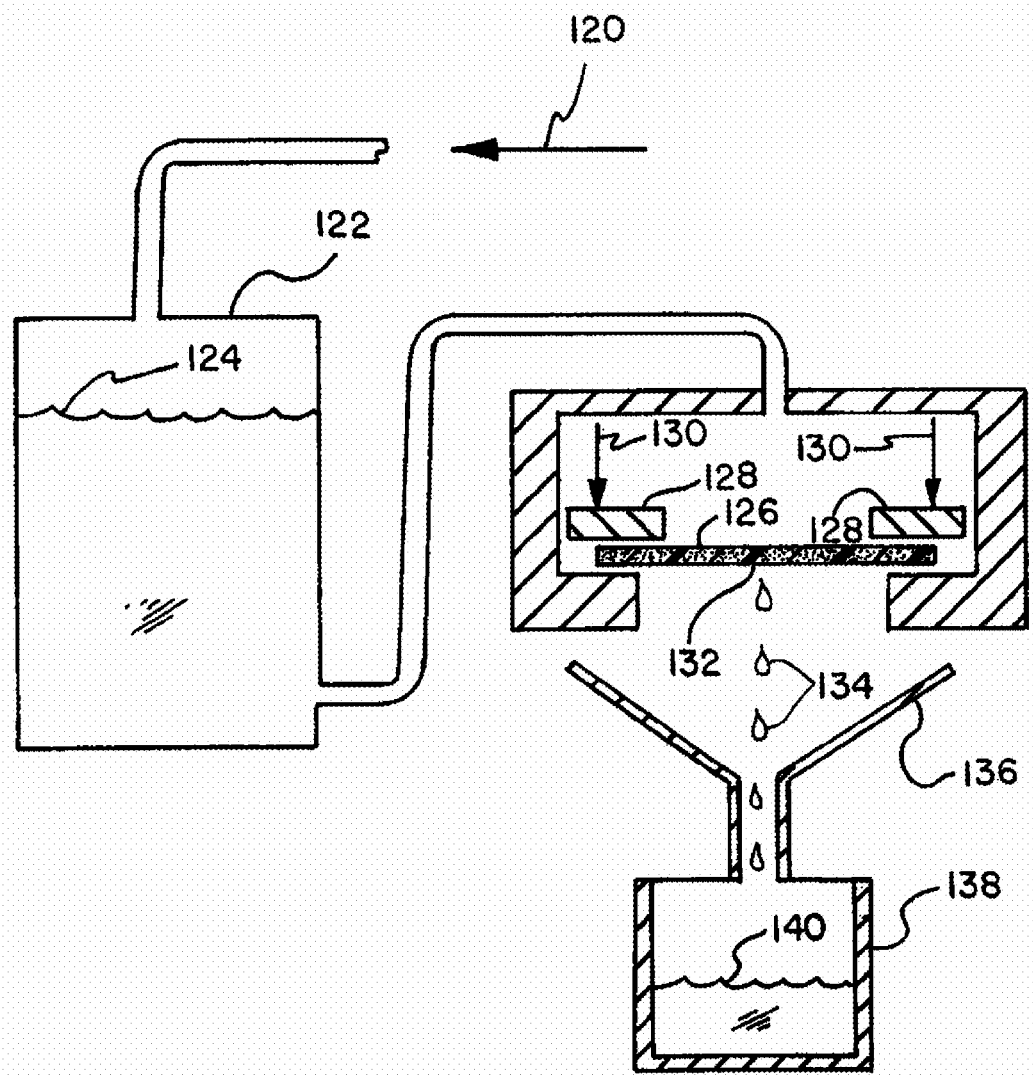
FIG. 17 is a side, cross sectional schematic view of a suture hole leak test apparatus adapted to evaluate various sheet materials of the present invention.

As shown in FIG. 17, an air over fluid reservoir 122, containing filtered, deionized water 124 is pressurized by applying air 120 at a constant 5.9 KPa. The water is maintained at a constant 40° C. The test sample is prepared by placing through the sample a specific number of sutures having a specific pattern. The prepared sample 126 is then positioned into a leak fixture. The sample 126 is clamped by a clamping ring 128, which is secured by clamping load 130. The constant water pressure, delivered to the upper surface of the test sample, forces water through the openings 132, created by the presuturing. Water droplets 134 are captured by a collection funnel 136 and directed into a graduated cylinder 138. The volume or weight of the collected water 140, over a specific amount of time, is used to calculate a leak rate, in ml/minute. This in vitro test defines the average water leak rate for a sample prepared in accordance with the following sample preparation procedure. The leak rate of various sample materials may be determined and compared using this test. The test sample 126 is prepared for the in vitro leak test according to FIG. 18.

Figure 18:
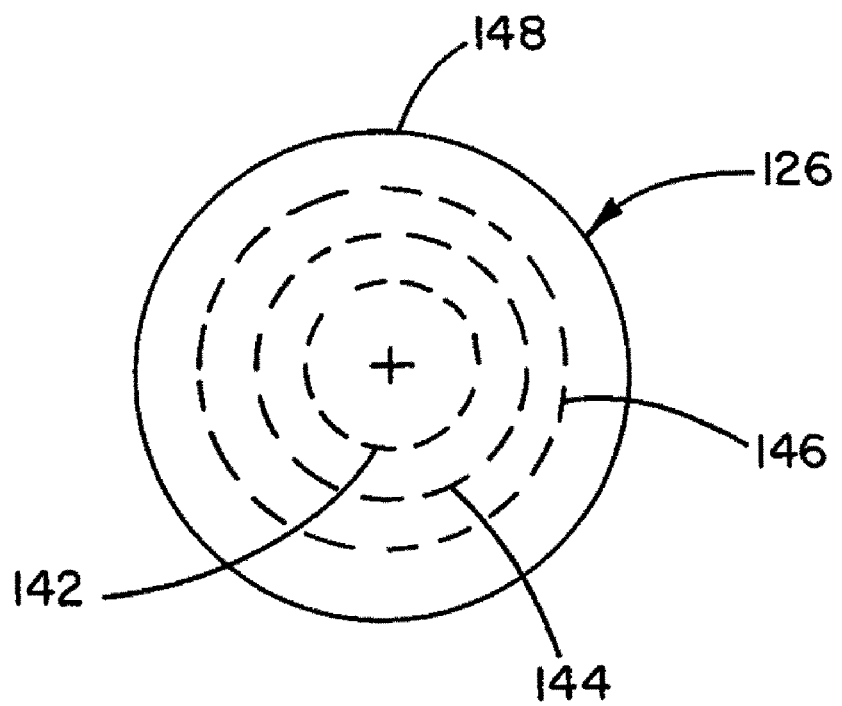
FIG. 18 is a top plan view of a sheet sample of the present invention adapted to be evaluated for suture hole leakage.
Figure 19:
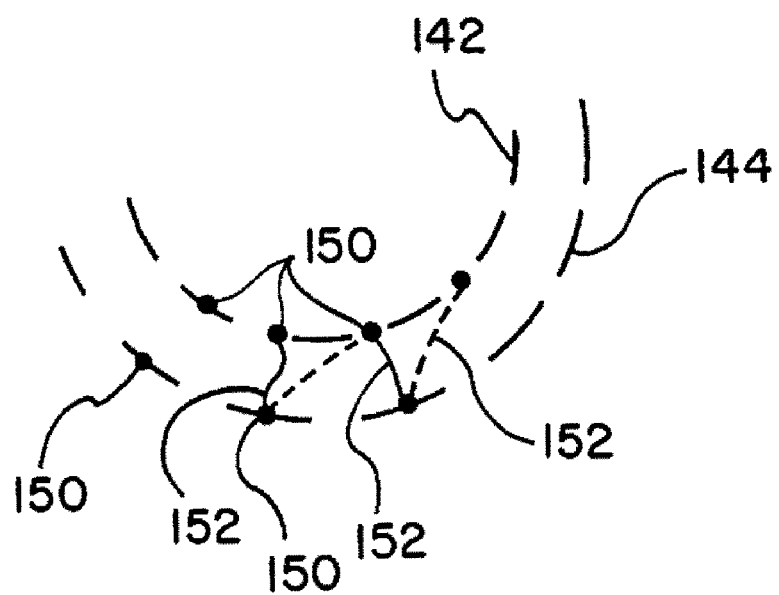
FIG. 19 is a partial top plan view of a suturing pattern employed in the sheet sample of FIG. 18.

Shown in FIG. 18 is a top view of the test sample 126. A continuous suture pattern is placed between the two diameters 142 and 144. The sample 126 is clamped between diameters 146 and 148. The diameter 142 is approximately 2.10 cm (0.08"), the diameter 144 is approximately 2.54 cm (1"), the diameter 146 is approximately 2.80 cm (1.1") and the diameter 148 is approximately 4.20 cm (1.65"). As shown in FIG. 19, a series of marks 150 are printed onto the sample. Forty marks 150 are printed, evenly spaced along each diameter 142 and 144. The marks 150 are paired or oriented in an approximate radial fashion, such that a line projected through a pair of marks crosses the approximate center of the sample. The sample is then sutured with a single 3-0 Braided Silk suture on a RB-1 needle (Ethicon Part Number K872H). Using the marks 150 as a guide, a continuous suture 152 is threaded through the sample and through a pair of marks without tension. The suture placement is continued, without tension through the sample and through all remaining marks. Upon completion of the pattern, the suture is knotted using four flat square throws.

Articles of the present invention, produced according to Example 1 and tested as previously described, had suture hole leak rates of less than about 30 ml/minute. Articles of the present invention can have suture hole leak rates, as defined by the previously described test, of less than about 25 ml/min, of less than about 30 ml/min, less than about 35 ml/min, less than about 40 ml/min, less than about 50 ml/min, less than about 70 ml/min, less than about 100 ml/min, less than about 200 ml/min, less than about 300 ml/min, or less than about 400 ml/min.

EXAMPLE 6

Figure 20:
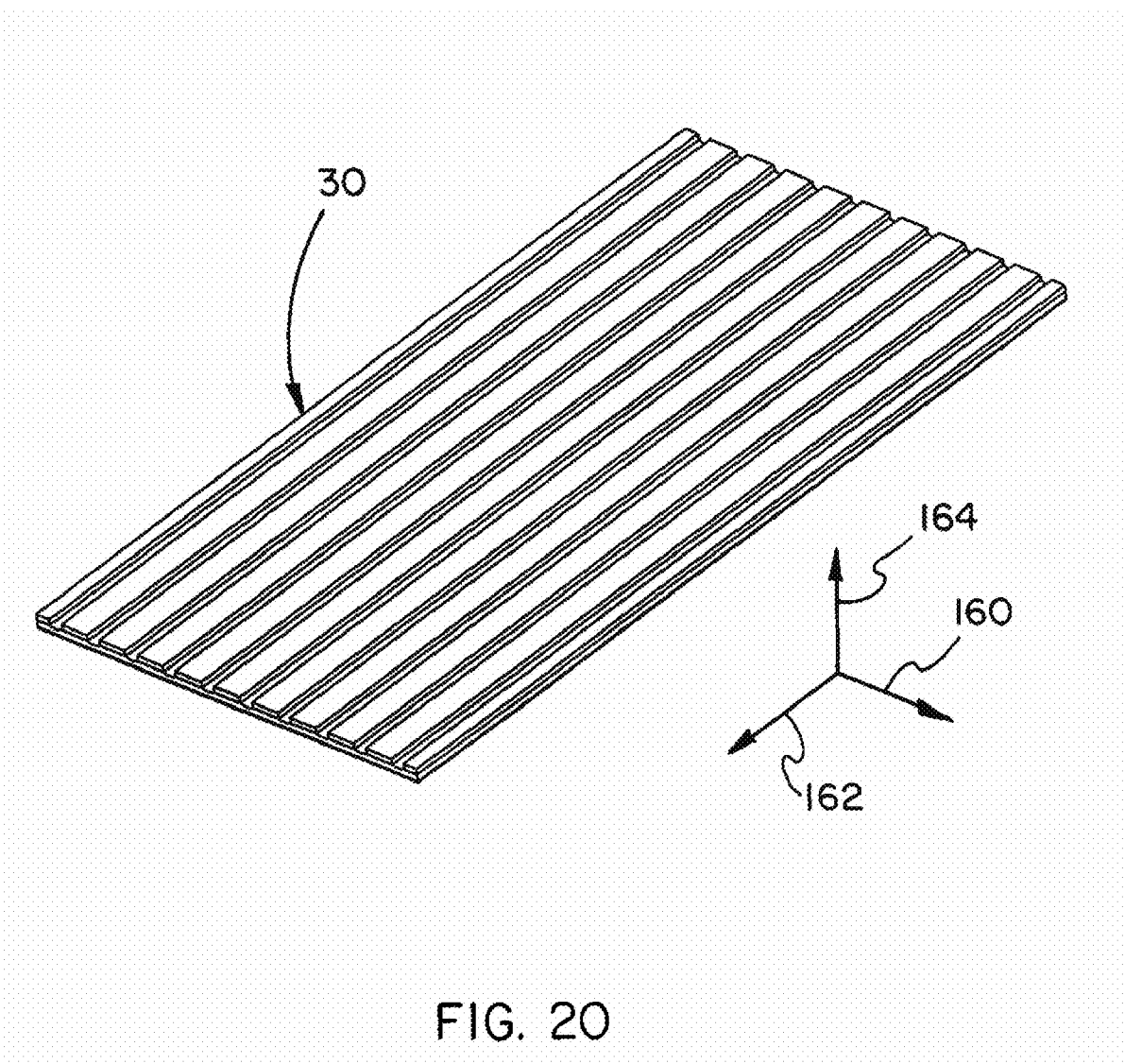
FIG. 20 is a three-quarter isometric view of an article of the present invention showing three orthogonal axis relating to the straining direction used to evaluate recovery properties of various materials.
Figure 21:
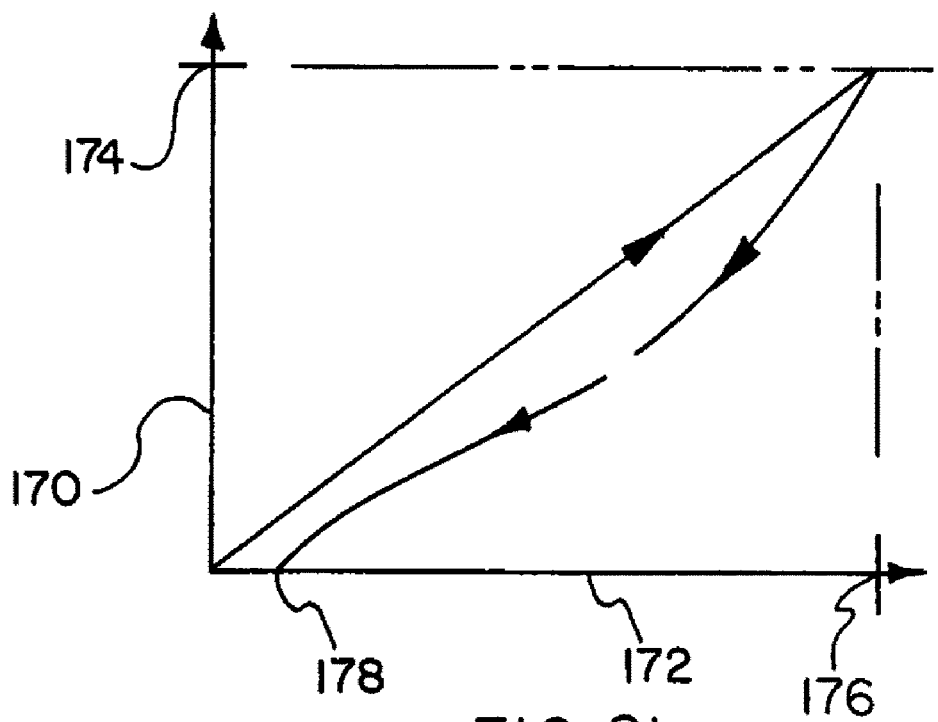
FIG. 21 is a graph plotting stress-strain of an article of the present invention, as strained along a first axis, displaying the amount of strain recovery.

Tensile tests were performed on articles of the present invention, produced in Example 1. Material samples were die cut into 7.6 cm by 1.3 cm strips, marked with 20 mm reference strain lines and evaluated on a Model 5564 tensile tester, available from Instron corp. (Canton, Mass.). A 2kN load cell was used along with and a Model 2603-080 extensometer with MERLIN™ software available from Instron corp. (Canton, Mass.). The die cut material samples were set to a 2.54 cm gage length, a 10 mm extensometer gage length and strained at a 250 mm/min rate. After being strained to about 100% of the initial gage length, the straining load was removed and the sample length was determined by the pre-marked reference strain lines. As shown in FIG. 20, an article 30 of the present invention has three orthogonal axes as defined by items 160, 162 and 164. Shown in FIG. 21 is a stress strain plot representing an article of Example 1, stressed along the axis 160. Shown is a vertical stress (MPa) axis 170, a horizontal strain (%) axis 172. The stress 174 at 100% strain 176 was about 5 MPa and the residual strain 178 was about 10%, equating to an approximate % recovery of about 90%.

Figure 22:
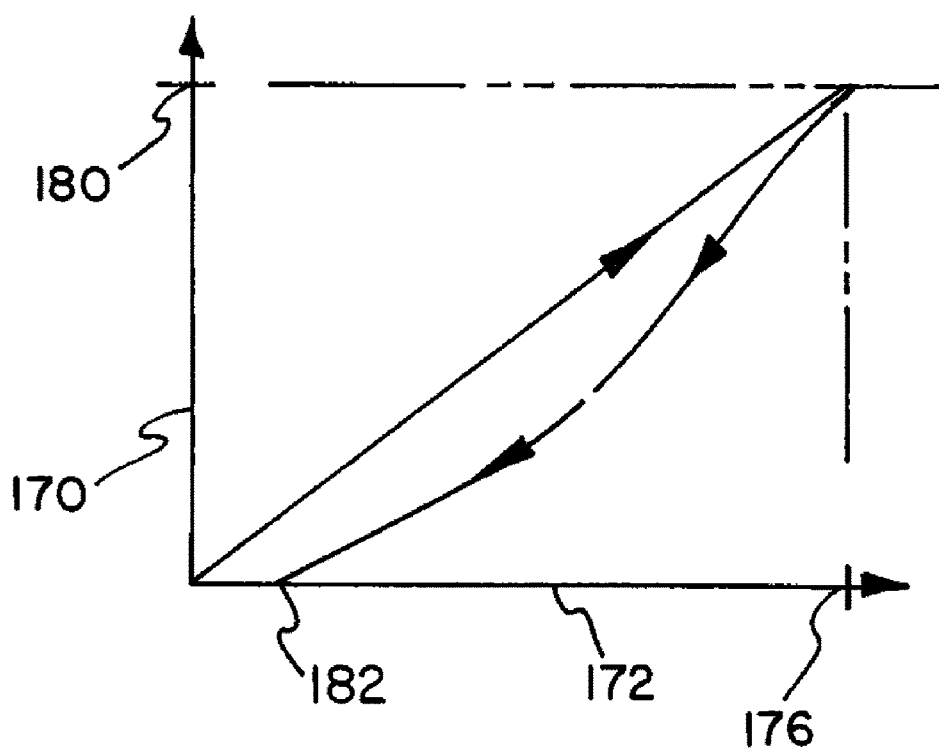
FIG. 22 is a graph plotting stress-strain of an article of the present invention, as strained along a second axis, displaying the amount of strain recovery.

Shown in FIG. 22 is a stress strain plot representing an article of Example 1, stressed along the axis 162. Shown is a vertical stress (MPa) axis 170, a horizontal strain (%) axis 172. The stress 180 at 100% strain 176 was about 10 MPa and the residual strain 182 was about 10%, equating to an approximate % recovery of about 90%.

EXAMPLE 7

A three-layer embodiment of the present invention, approximately 5 cm (2") by 6 cm (2.4"), was constructed by providing a laminated precursor material having a first layer of ePTFE, a second layer of an elastomeric fluoropolymer and a third layer of ePTFE. The precursor material is commercially available as PRECLUDE® Dura Substitute, Part Number 1PDX301, from W. L. Gore & Associates, Inc. (Flagstaff, Ariz.). The precursor sheet was then positioned onto a laser (as described in FIG. 7) to create a pattern of discontinuities and macroscopic roughness into the first layer of the laminated sheet. The precursor sheet periphery was constrained by a ringed pin fixture. The laser was a Laser Machining Inc. (Somerset, Wis.), CO₂ Eagle 500 Laser with Lightening Bolt Control Software. The laser was adjusted to have an output of about 160 W, a −0.4125 focus, cutting traverse speed of about 70 cm/sec (27 in/sec). The pattern of discontinuities was as shown in FIG. 1. The discontinuities were approximately 0.5 mm (0.02") wide and spaced approximately 0.13 mm (0.05") from center to center. The completed article was about 0.3 mm (0.012") thick.

EXAMPLE 8

A three-layer embodiment of the present invention, approximately 3 cm (1.2") by 6 cm (2.4"), was constructed by providing a laminated precursor material having a first layer of ePTFE, a second layer of an elastomeric fluoropolymer and a third layer of ePTFE. The precursor material is commercially available as GORE-TEX® ACUSEAL™ Cardiovascular Patch, Part Number 1CVX101, from W. L. Gore & Associates, Inc. (Flagstaff, Ariz.). The precursor sheet was then positioned onto a laser (as described in FIG. 7) to create a pattern of discontinuities and macroscopic roughness into the first layer of the laminated sheet. The precursor sheet periphery was constrained by a ringed pin fixture. The laser was a Laser Machining Inc. (Somerset, Wis.), $CO_2$ Eagle 500 Laser with Lightening Bolt Control Software. The laser was adjusted to have an output of about 160 W, a −0.4125 focus, cutting traverse speed of about 70 cm/sec (27 in/sec). The pattern of discontinuities was as shown in FIG. 1. The discontinuities were approximately 0.5 mm (0.02") wide and spaced approximately 0.13 mm (0.05") from center to center. The completed article was about 0.5 mm (0.02") thick.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A surgically implantable article, comprising:
   a first layer of multiple adjacent non-bioabsorbable polymer structures formed from a continuous non-bioabsorable polymer layer; and
   a second layer of elastomer arranged on the first layer,
   wherein the adjacent non-bioabsorbable polymer structures in the first layer are macroscopically discontinuous, being separated from each other by the elastomer.

2. The surgically implantable article of claim 1, wherein the first layer has a pattern of discontinuities.

3. The surgically implantable article of claim 2, wherein the pattern of discontinuities is a linear pattern.

4. The surgically implantable article of claim 2, wherein the pattern of discontinuities is a crosshatch pattern.

5. The surgically implantable article of claim 1, wherein the first layer is macroscopically rough.

6. The surgically implantable article of claim 1, wherein the article self seals when sutured.

7. The surgically implantable article of claim 1, wherein the article is resistant to suture hole leakage.

8. The surgically implantable article of claim of claim 1, wherein the first discontinuous layer comprises ePTFE.

9. The surgically implantable article of claim 1, wherein the article comprises a third layer of a polymer.

10. The surgically implantable article of claim 9, wherein the third layer substantially prevents tissue in-growth.

11. The surgically implantable article of claim 10, wherein said polymer comprises ePTFE, said ePTFE having an average fibril length of less than about 5 μm.

12. The surgically implantable article of claim 1, wherein the first discontinuous layer allows for tissue in-growth.

13. A dura mater substitute, comprising:
    a first layer of multiple adjacent non-bioabsorbable polymer structures formed from a continuous non-bioabsorable polymer layer that allows for native dura mater in-growth;
    a second layer of elastomer arranged on the first layer, wherein the adjacent non-bioabsorbable polymer structures in the first layer are macroscopically discontinuous, being separated from each other by the elastomer; and
    a third layer that substantially prevents tissue in-growth.

14. The dura mater substitute of claim 13, wherein the first layer has a pattern of discontinuities.

15. The dura mater substitute of claim 14, wherein the pattern of discontinuities is a linear pattern.

16. The dura mater substitute of claim 14, wherein the pattern of discontinuities is a crosshatch pattern.

17. The dura mater substitute of claim 13, wherein the first layer is macroscopically rough.

18. The dura mater substitute of claim 13, wherein said dura mater substitute is resistant to suture hole leakage.

19. The dura mater substitute of claim 13, wherein the first discontinuous layer comprises ePTFE.

20. The dura mater substitute of claim 13, wherein said third layer comprises ePTFE, said ePTFE having an average fibril length of less than about 5 μm.

* * * * *